(12) United States Patent
El Sayyid et al.

(10) Patent No.: US 6,331,252 B1
(45) Date of Patent: Dec. 18, 2001

(54) METHODS FOR PRIMING A BLOOD COMPARTMENT OF A HEMODIALYZER

(75) Inventors: Waleed Mutasem El Sayyid, Miami; Cameron Scott Casterline, Pembrooke Pines, both of FL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/126,761

(22) Filed: Jul. 31, 1998

(51) Int. Cl.[7] .................................................. B01D 61/00
(52) U.S. Cl. ....................... 210/646; 210/650; 210/739; 210/929
(58) Field of Search .................................... 210/645, 646, 210/647, 650, 739, 929, 321.65, 321.71, 252, 257.2, 258; 604/4, 5, 6, 4.01, 5.01

(56) References Cited

U.S. PATENT DOCUMENTS

| | | | |
|---|---|---|---|
| 3,946,731 | 3/1976 | Lichtenstein | 210/90 |
| 4,021,341 | 5/1977 | Cosentino et al. | 210/103 |
| 4,172,033 | 10/1979 | Willock | 210/85 |
| 4,334,988 | 6/1982 | Milligan | 210/87 |
| 4,486,303 | 12/1984 | Brous | 210/87 |
| 4,585,552 | 4/1986 | Gummesson et al. | 210/87 |
| 4,708,802 | 11/1987 | Rath et al. | 210/641 |
| 4,747,950 | 5/1988 | Guinn | 210/646 |
| 4,879,040 | 11/1989 | Prince et al. | 210/637 |
| 4,966,691 | 10/1990 | Brous | 210/87 |
| 5,211,849 | 5/1993 | Kitaevich et al. | 210/645 |
| 5,247,434 | 9/1993 | Peterson et al. | 210/646 |
| 5,336,165 | * 8/1994 | Twardowski | 604/5 |
| 5,484,397 | 1/1996 | Twardowski | 604/5 |
| 5,490,925 | 2/1996 | Eigendorf | 210/321.69 |
| 5,702,606 | * 12/1997 | Peter, Jr. et al. | 210/646 |
| 5,744,027 | * 4/1998 | Connell et al. | 210/96.2 |
| 5,792,367 | * 8/1998 | Mattisson et al. | 210/741 |
| 5,863,421 | 1/1999 | Peter, Jr. et al. | 210/134 |
| 5,932,103 | 8/1999 | Kenley et al. | 210/646 |
| 6,132,616 | * 10/2000 | Twardowski et al. | 210/646 |

FOREIGN PATENT DOCUMENTS

| | | |
|---|---|---|
| 212 648 | 8/1984 | (DE) . |
| 240 137 | 10/1986 | (DE) . |
| 36 00 227 | 7/1987 | (DE) . |
| 0715859 A1 | 6/1996 | (EP) . |
| 2 368 283 | 5/1978 | (FR) . |
| 2 368 963 | 5/1978 | (FR) . |
| 2 414 351 | 8/1979 | (FR) . |

\* cited by examiner

*Primary Examiner*—John Kim
(74) *Attorney, Agent, or Firm*—Paula J. Kelly; Charles R. Mattenson; Robert M. Barrett

(57) ABSTRACT

A method for priming a hemodialyzer is disclosed. Hemodialyzer comprises a dialysate compartment, a blood compartment, and a dialysis membrane separating the dialysate and blood compartments. The method comprises the steps of delivering a liquid to a dialysate inlet of the dialysate compartment at a first volumetric delivery rate, passing the liquid through the dialysate compartment from the dialysate inlet to a dialysate outlet of the hemodialyzer and delivering the liquid from the dialysate outlet at a second volumetric delivery rate that is less than the first volumetric delivery rate so as to cause a net flow of the liquid from the dialysate compartment to the blood compartment through the dialysis membrane.

16 Claims, 2 Drawing Sheets

METHODS FOR PRIMING A BLOOD COMPARTMENT OF A HEMODIALYZER

FIELD OF THE INVENTION

The present invention pertains to hemodialysis (artificial kidney) apparatus and related methods. More specifically, the invention pertains to such apparatus and methods as used for controlling ultrafiltration of fluid from a patient.

BACKGROUND OF THE INVENTION

Practical hemodialysis made its debut in the early 1960s with the essentially simultaneous advent of hemodialysis apparatus capable of producing dialysate on line and of hemodialyzers exhibiting an acceptable reliability. Since then, great developments have occurred in hemodialyzers and in hemodialysis apparatus.

Nephrology clinicians have long appreciated the need for hemodialysis to remove not only toxic metabolic solutes from the blood but also excess fluid. Removal of fluid across the semipermeable hemodialysis membrane is termed "ultrafiltration".

The ongoing development of improved hemodialysis membranes has been driven in part by the clinical need to perform ultrafiltration (along with hemodialysis) of a patient in a manner that alleviates patient morbidity as much as possible. With respect to ongoing improvements in hemodialysis membranes, the general trend has been to produce membranes having increased "flux" by which is meant water permeability. Such membranes achieve a more rapid ultrafiltration of water from the blood at a lower transmembrane pressure (TMP). The overarching requirements of safety and well-being for the patient being treated with such membranes have driven the development of hemodialysis apparatus that provide excellent control of ultrafiltration. Such development has been the subject of intensive research by individuals and corporate entities working in the hemodialysis field.

A notable example of a hemodialysis apparatus that provides control of ultrafiltration is disclosed in U.S. Pat. No. 5,247,434 to Peterson et al., which is incorporated herein by reference.

Another trend in hemodialysis has been various approaches to achieving more rapid dialysis (with ultrafiltration) without adversely affecting patient morbidity. According to some approaches, this is achieved by, inter alia, passing dialysate through the hemodialyzer at a higher flow rate than conventionally. In this regard, the conventional dialysate flow rate is 500 mL/min, and some modern dialysis apparatus can achieve a dialysate flow rate of about 1000 mL/min. However, some clinicians perceive a need for dialysate flow rates of 3000–4000 mL/min.

Such increased dialysate flow rates impose a need to achieve greater ultrafiltration rates than conventionally. For example, whereas conventional dialysis apparatus typically achieve an ultrafiltration rate up to about 4000 mL/hr, some clinicians perceive a need for ultrafiltration rates of up to 10 L/hr.

Despite great advances in the art of clinical ultrafiltration, especially ultrafiltration performed during a hemodialysis treatment, conventional apparatus are limited in their ability to satisfy the needs summarized above.

SUMMARY OF THE INVENTION

According to a first aspect of the invention, hemodialysis apparatus are provided that prepare fresh dialysate and deliver the dialysate from a mix chamber to a hemodialyzer and return spent dialysate from the hemodialyzer to a drain. A preferred embodiment of such an apparatus comprises, in hydraulic order, a first positive-displacement pump, a first flowmeter, a second flowmeter, and a second positive displacement pump. The first positive-displacement pump has an inlet hydraulically connected to the mix chamber. The first flowmeter has an inlet hydraulically connected to an outlet of the first pump and an outlet hydraulically connectable to a dialysate inlet of a hemodialyzer. The first flowmeter produces a respective output having a characteristic that is a function of a volumetric pumping rate of the first pump. The second flowmeter has an inlet hydraulically connectable to a dialysate outlet of the hemodialyzer. The second positive-displacement pump has an inlet hydraulically connected to an outlet of the second flowmeter and an outlet hydraulically connected to a drain. The second flowmeter produces a respective output having a characteristic that is a function of a volumetric pumping rate of the second pump. The first and second pumps define therebetween a UF loop, wherein a difference in the volumetric pumping rate of the second pump relative to the volumetric pumping rate of the first pump generates a volumetric condition in the UF loop that urges a net ultrafiltration of fluid across a semipermeable membrane in the hemodialyzer. Preferably, the first and second pumps are gear pumps.

The respective outputs of the first and second flowmeters preferably comprise respective electrical signals. The electrical signals preferably exhibit a respective characteristic from which a difference in the respective signals can be determined, wherein the difference can be used to govern the relative pumping rates of the first and second pumps. To such end, the first and second pumps as well as the first and second flowmeters can be electrically connected to a suitable processor or computer that performs such determinations and provides feedback control signals to the first and second pumps so as to achieve, for example, a desired rate of ultrafiltrate removal from a blood compartment to a dialysate compartment of the hemodialyzer, or (if desired) a "zero-UF" operating condition resulting in zero net flow of liquid from the blood compartment to the dialysate compartment or from the dialysate compartment to the blood compartment.

With respect to achieving ultrafiltration from the blood compartment to the dialysate compartment, the volumetric pumping rate of the second pump is set greater than the volumetric pumping rate of the first pump. The resulting volumetric imbalance of dialysate entering the dialysate compartment versus dialysate exiting the dialysate compartment results in a net ultrafiltration of liquid from the blood compartment to the dialysate compartment.

A "reverse ultrafiltration" condition can be achieved by operating the first pump to have a volumetric pumping rate that is greater than the volumetric pumping rate of the second pump. The resulting volumetric imbalance causes a net ultrafiltration of liquid from the dialysate compartment to the blood compartment.

According to another aspect of the invention, methods are provided for performing ultrafiltration of a liquid passing through the blood compartment of a hemodialyzer. According to a preferred embodiment of such a method, a dialysate solution is provided. While passing the liquid through the blood compartment of the dialyzer, the dialysate solution is conducted through a first positive displacement pump, then through a first flowmeter, then to a dialysate inlet of a dialysate compartment of the hemodialyzer. The first pump delivers the dialysate to the dialysate inlet at a first volumetric pumping rate as measured by the first flowmeter. After passing the dialysate through the dialysate compartment, the dialysate is conducted from an outlet of the dialysate compartment through a second flowmeter, then through a second positive displacement pump. The second pump pumps the dialysate at a second volumetric pumping rate, as measured by the second flowmeter, that is greater than the pumping rate of the first pump. The resulting volumetric imbalance urges an ultrafiltrate liquid to pass from the blood compartment to the dialysate compartment.

To provide the dialysate, a dialysate concentrate can be added to a water stream at a proportioning ratio that is a function of the volumetric pumping rate of the first pump as measured by the first flowmeter.

According to another aspect of the invention, methods are provided for priming a blood compartment of a hemodialyzer. According to a preferred embodiment of such a method, first a liquid is provided. The liquid is conducted through a first positive displacement pump, then through a first flowmeter, then to a dialysate inlet of a dialysate compartment of the hemodialyzer. The first pump delivers the liquid to the dialysate inlet at a first volumetric pumping rate as measured by the first flowmeter. After passing the liquid through the dialysate compartment, the liquid is conducted from an outlet of the dialysate compartment through a second flowmeter, then through a second positive displacement pump. The second pump pumps the liquid at a second volumetric pumping rate, as measured by the second flowmeter, that is less than the pumping rate of the first pump so as to urge net flow of the liquid from the dialysate compartment to the blood compartment of the hemodialyzer. Preferably, the liquid used for priming is a dialysate solution, thereby eliminating a need to use expensive isotonic saline solution. The liquid passing from the dialysate compartment to the blood compartment can also be passed through blood lines connected to the blood compartment of the hemodialyzer so as to prime the blood lines in addition to the hemodialyzer.

The foregoing and additional features and advantages of the invention will be more readily apparent from the following detailed description, which proceeds with reference to the accompanying drawings.

DETAILED DESCRIPTION

The following detailed description is directed to the current best mode of the invention, but is not to be regarded as limiting in any way.

The hydraulic system of most hemodialysis apparatus comprises the following principal components (in hydraulic order): an incoming water pressure regulator and a water heater with safety thermostat that serve to produce a warm water stream at a particular flow rate; a first concentrate pump that delivers a stream of "A" concentrate into the water stream at a predetermined flow rate relative to the water flow rate to produce a stream of diluted "A" concentrate; a deaeration chamber with air-removal pump and vented air trap for removing dissolved gas from the stream of diluted "A" concentrate; an "A" conductivity probe for determining whether the "A" concentrate has been properly diluted; a second concentrate pump that delivers a stream of "B" concentrate into the water stream at a predetermined flow rate relative to the flow rates of water and "A" concentrate to produce a dialysate solution; a "B" mix chamber and conductivity probe to achieve thorough mixing of the concentrates with the water and for determining whether the dialysate is at a proper ionic strength; the hemodialyzer; a blood-leak detector; and a drain line. By way of example, reference is made to the above-cited U.S. Pat. No. 5,247,434 (the "'434 patent"), incorporated herein by reference, specifically FIGS. 1A–1B of that patent and the accompanying description, for a depiction and description of these components.

To achieve ultrafiltration in a controlled manner, the hydraulic circuit disclosed in the '434 patent utilizes a "flow equalizer" comprising "pre-dialyzer" and "post-dialyzer" chambers, multiple inlet and outlet valves, and pressure regulators. The flow equalizer is situated in the hydraulic circuit between the "B" mix chamber and the blood-leak detector (see FIGS. 1A–1B of the '434 patent in which the flow equalizer is denoted by the reference number 54, the "B" mix chamber is denoted by the reference number 44, and the blood-leak detector is denoted by the reference number 78). Experience has shown that the flow equalizer in the '434 patent, and similar devices found in many other contemporary hemodialysis apparatus, is expensive to manufacture and is limited in terms of an achievable range of dialysate flow rate and of ultrafiltration rate.

Hence, according to one aspect of the present invention, an ultrafiltration-control apparatus is provided that is intended to be inserted into the hydraulic circuit of a hemodialysis apparatus between the "B" mix chamber and the blood-leak detector and replace the "flow equalizer" or similar device found in contemporary hemodialysis apparatus.

Figure 1:
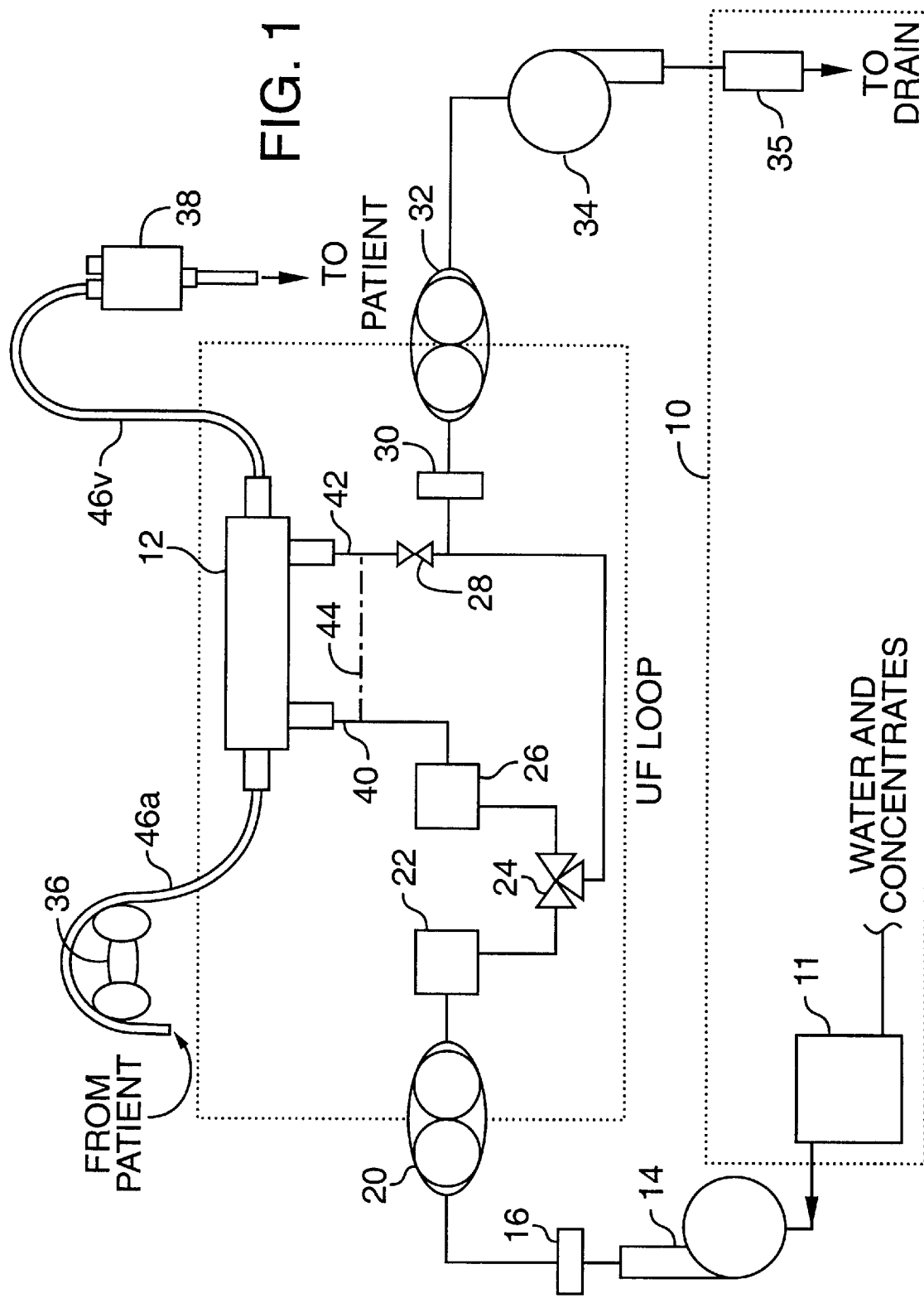
FIG. 1 is a schematic diagram of a portion of the hydraulic circuit of a hemodialysis apparatus according to the present invention.

In FIG. 1 of the present disclosure, the hydraulic circuit of the hemodialysis apparatus including the "B" mix chamber 11 (and components upstream thereof) and the blood-leak detector 35 (and components downstream thereof) is denoted by the block 10. The hydraulic circuitry in the block 10 functions to prepare a continuous stream of dialysate by appropriately mixing "A" and "B" concentrates into a water stream at a particular dialysate flowrate, temperature (nominally 37° C.), concentration (as measured, e.g., conductometrically), and pressure for delivery to a hemodialyzer 12. The hydraulic circuitry in the block 10 also receives spent dialysate from the hemodialyzer 12, passes the spent dialysate through the blood-leak detector 35 (as a way of monitoring the structural integrity of the dialyzer membrane), and delivers the spent dialysate to a drain for disposal.

From the "B" mix chamber 11, fresh dialysate enters a first positive displacement pump (e.g., gear pump, also termed a "pre-dialyzer pump") 14. Dialysate exiting the first pump 14 passes through a filter 16 (to remove suspended particulates) and enters a "UF loop" 18. The UF loop 18 comprises a first flow meter 20 (also termed a "pre-dialyzer flow meter"), a conductivity probe 22, a bypass valve 24, a flow sensor/pressure transducer 26, the hemodialyzer 12, a two-way valve 28, a filter 30, and a second flow meter 32 (also termed a "post-dialyzer flow meter"). The dialysate passes through the pre-dialyzer flow meter 20, the conductivity probe 22, the bypass valve 24, and the flow sensor/ pressure transducer 26 before entering the hemodialyzer 12. As is generally known, the dialysate passes through a "dialysate compartment" of the hemodialyzer as the dialysate flows from one end of the hemodialyzer to the other. After passing through the hemodialyzer 12, the dialysate is termed "spent" dialysate. The spent dialysate passes through the two-way valve 28, the filter 30, and the post-dialyzer flow meter 32 to exit the UF loop 18. The spent dialysate then passes through a second positive displacement pump (e.g., gear pump; also termed a "post-dialyzer pump") 34 to the blood-leak detector 35.

As generally known, the hemodialyzer 12 also has a "blood compartment" that is separated from the dialysate compartment by the semipermeable dialysis membrane. During use of the hemodialyzer 12, extracorporeal blood from a patient passes through a blood pump 36 and through an "arterial" blood line 46a to the blood compartment of the hemodialyzer 12. As the extracorporeal blood passes through the blood compartment, metabolic solutes and excess water are removed from the blood by passing from the blood to the dialysate flowing through the dialysate compartment. Thus the blood is "treated". "Treated" blood exits the hemodialyzer 12 through a "venous" blood line 46v and drip chamber 38 (normally provided in an extracorporeal blood- tubing set) before being returned to the patient. The drip chamber 38 is the locus of blood-pressure measurements.

The pre- and post-dialyzer pumps 14, 34, respectively, not only deliver fresh dialysate to and remove spent dialysate from the hemodialyzer 12, respectively, but also control the amount of water (ultrafiltrate) removed from the patient. The rate at which the ultrafiltrate is removed from the patient is equal to the difference, if any, in the dialysate flow rate through the pre-dialyzer pump 14 versus the dialysate flow rate through the post-dialyzer pump 34. More specifically, if these dialysate flow rates are equal, then no net ultrafiltration occurs; if the flow rate of the post-dialyzer pump 34 is greater than the flow rate of the pre-dialyzer pump 14, then ultrafiltration of the blood passing through the blood compartment occurs at a rate equal to the difference in flow rates of the pre- and post-dialyzer pumps 14, 34, respectively. If the flow rate of the pre- dialyzer pump 14 is greater than the flow rate of the post-dialyzer pump 34, then a net movement of fluid occurs from the dialysate to the blood across the dialysis membrane.

The pre- and post-dialyzer flow meters 20, 32 are used to measure and provide an indication of the actual dialysate flow rate through the pre- and post-dialyzer pumps 14, 34, respectively. The difference in flow rates measured by the pre- and post-dialyzer flow meters 20, 32 provide a measurement of the ultrafiltration rate.

As disclosed by way of example in the '434 patent, dialysate is produced by an on-line proportioning system comprising two fixed-volume pumps (e.g., piston pumps) for pumping dialysate concentrates at respective flow rates at respective ratios relative to the flow rate measured by the pre-dialyzer flow meter 14. A conductivity probe is located at each of three locations: the "A" mix chamber, the "B" mix chamber 11, and just downstream of the pre-dialyzer flow meter 20.

The filters 16, 30 upstream of the respective flow meters serve to remove large particulates from the dialysate and thus prevent such particulates from entering the respective flow meters where such particulates could otherwise affect the accuracy of the flow meters 20, 32.

The two-way valve 28 is preferably automatically actuatable to prevent cross flow of dialysate from or to the dialysate compartment of the hemodialyzer 12 during events such as calibration of the hemodialysis apparatus, bypass, and/or alarm conditions.

The flow meters 20, 32 can be any of various types such as, for example, laminar-flow types, turbine types, and gear types. By way of example and not intended to be limiting in any way, representative types include: Model ZDM positive-displacement gear flowmeter manufactured by Kobold; various flowmeters manufactured by Alicat Scientific Inc., Tucson, Ariz. including Models PVM and M12 laminar flow flowmeters, Models PVL and L12 volumetric flowmeters, Models PVUL and UL12 liquid flowmeters, Model TFM turbine flowmeters, and Model TVM turbine flowmeters; and Models DFS-2 and DFS-2W turbine flowmeters manufactured by Digiflow Systems. Preferably, the flow meters 20, 32 provide a measurement accuracy of at least +/−0.5% and a precision of at least +/−0.1%.

The pre- and post-dialyzer pumps 14, 34 are preferably gear pumps (e.g., but not limited to, Model 3002Q1TT manufactured by XOLOX, Fort Wayne, Ind.) exhibiting a sufficiently low back flow to be considered "positive displacement". However, any of various models of, e.g., vane pumps and piston pumps can be used. The pumps 14, 34 are preferably capable of delivering a dialysate flow rate through the hemodialyzer 12 within a range of 100 mL/min to 4000 mL/min.

The hemodialyzer 12 is connected into the "UF loop 38 by dialysate lines 40, 42. Whenever the hemodialyzer 12 is not being used (e.g., when the dialysis apparatus is being rinsed), the dialysate lines are connected to a "rinse block" 44 that is simply a conduit allowing dialysate flow to bypass the hemodialyzer 12.

Before beginning a dialysis treatment, the dialysate lines 40, 42 are typically connected to the rinse block 44. The pre- and post-dialyzer pumps 14, 34 are run simultaneously at the same speed (same pump rate) at a desired dialysate flow rate for rinsing, as indicated by the flow meters 20, 32. The flow meters 20, 32 are preferably connected to a processor (see, e.g., the '434 patent disclosure) that calibrates, by execution of appropriate software, the two flow meters 20, 32 relative to the respective speeds of the pumps 14, 34. I.e., whenever the pumps 14, 34 are running at exactly the same speed, the processor calibrates the flow meters 20, 32 to have the same flow reading.

In preparation for performing dialysis, the hemodialyzer 12 is connected to the dialysate lines 40, 42. Also, the dialyzer 12 is connected to the patient via the "arterial" blood line 46a and the "venous" blood line 46v. To facilitate priming of the blood lines 46a, 46v and of the blood compartment of the hemodialyzer 12, the pre-dialyzer pump 14 can be operated at a speed greater than the speed of the post-dialyzer pump 34. This urges passage of dialysate from the dialysate compartment to the blood compartment of the hemodialyzer 12 and thus eliminates the conventional need to consume a bag of isotonic saline for priming.

For the impending dialysis treatment (or during treatment), the operator elects a desired ultrafiltration volume to be achieved. The operator enters such data, along with data concerning the dialysate flow rate to be used during the treatment, into the processor (see, e.g., the '434 patent which discloses entering data using a touch screen). The processor determines, in view of the dialysate flow rate, the ultrafiltration rate required to achieve the desired ultrafiltration volume. Based on such a determination, the processor controls the relative speeds of the pre- and post-dialyzer pumps (typically the post-dialyzer pump 34 runs at a faster speed than the pre-dialyzer pump 14 to perform ultrafiltration) during the treatment. The actual rate of ultrafiltration is the difference in flow rates indicated by the preand post-dialyzer flow meters 20, 32. Such data can be processed by the processor to provide an indication of the actual ultrafiltration rate.

At any time during operation, such as during an actual treatment, the pre-dialyzer flow meter provides a reading of dialysate flow rate that is the reference for determining the rate at which the "A" and "B" concentrate pumps deliver "A" and "B" concentrate, respectively, to the water stream. I.e., the "A" and "B" concentrate pumps deliver the respective concentrates at respective fixed ratios of the pre-dialyzer dialysate flow rate.

At the conclusion of the treatment, the apparatus is placed in "bypass" (thereby diverting dialysate flow around the hemodialyzer 12). The post-dialyzer pump 34 slows down to the speed of the pre-dialyzer pump 14 and the dialysate pressure is thus maintained at around atmospheric pressure.

Apparatus according to the invention eliminate a need for a "UF-removal pump" as used in contemporary hemodialysis apparatus for removing ultrafiltrate (UF). Specifically, contemporary hemodialysis apparatus that perform ultrafiltration control employ a "flow equalizer" or analogous component to establish a baseline condition in which volumetric flow of dialysate into the hemodialyzer is exactly equal to the volumetric flow of dialysate out of the hemodialyzer (termed a "zero-UF" condition). Any ultrafiltration is achieved by employing a UF-removal pump to remove fluid, relative to the baseline condition, that must be replaced by net movement of fluid from the blood compartment to the dialysate compartment of the hemodialyzer. An apparatus according to the present invention, in contrast, does not rely upon a constant baseline (zero-UF) condition. Rather, by simply changing the speed of one of the pumps 14, 34 relative to the other, a condition can be established in the dialysate compartment urging net flow of liquid from the blood compartment to the dialysate compartment or from the dialysate compartment to the blood compartment.

It is also noted that contemporary dialysis apparatus relying upon a flow equalizer cannot produce a condition favoring net passage of liquid from the dialysate compartment to the blood compartment (a so-called "reverse-ultrafiltration" condition). Apparatus according to the present invention, in contrast, can achieve a reverse-ultrafiltration condition (as used, e.g., for priming as described above) by simply causing the pre-dialyzer pump 14 to operate at a faster speed than the post-dialyzer pump 34.

Working Example

Figure 2:
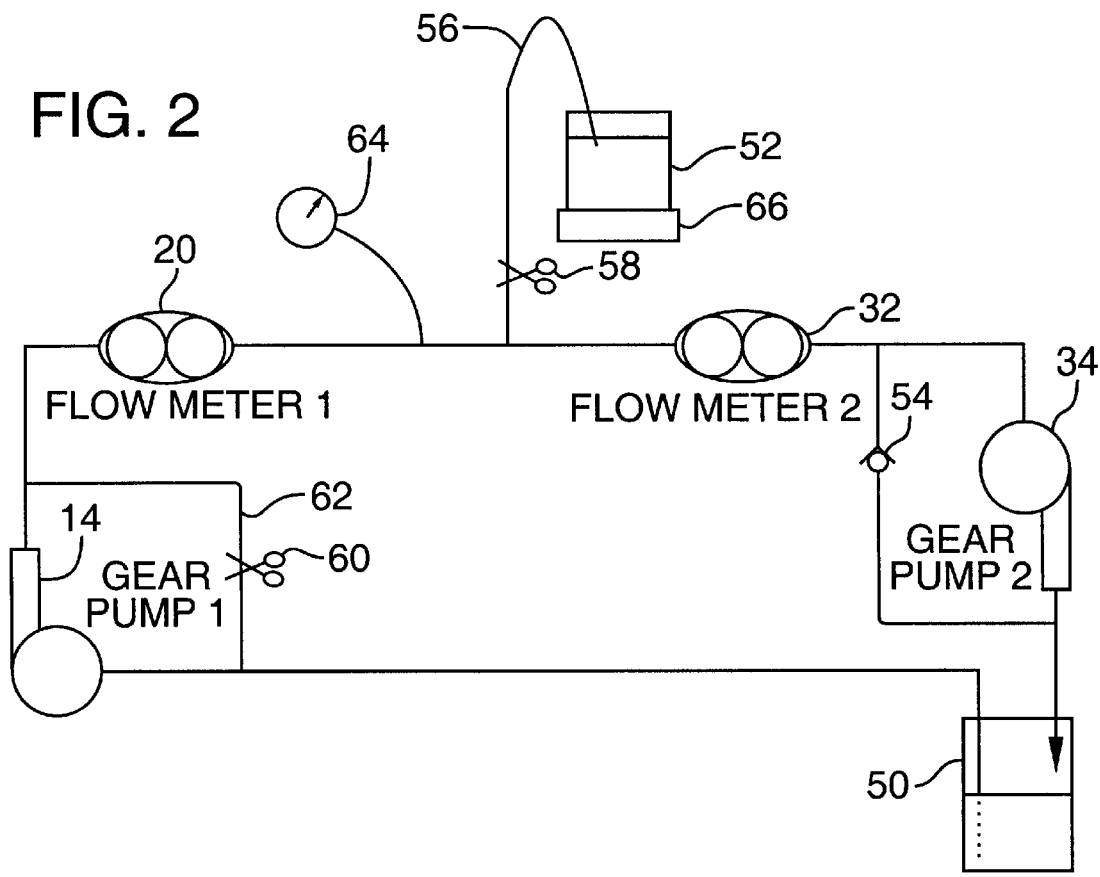
FIG. 2 is a schematic diagram of the hydraulic circuit that was the subject of the Working Example.

A test setup as shown in FIG. 2 was constructed. The test setup comprised a first liquid vessel 50 and a second liquid vessel 52, as well as the first and second pumps 14, 34 and first and second flowmeters 20, 32. Each of the pumps 14, 34 was powered by 24 VDC, and the speed of each pump was controlled by a separate 0–5 VDC power supply. The speed of each pump 14, 34 was continuously recorded. The flowmeters 20, 32 were powered by separate 12 VDC power supplied. Indicated flowrates were continuously recorded. To begin, the line 56 was clamped using a first hemostat 58, and a second hemostat 60 was removed from the line 62. Both pumps 14, 34 were run at 600 RPM (20 Hz, representing a "zero-UF" condition) for a period of time (1 minute) to ascertain the ability of the system to provide consistent zero-UF performance. Ten identical trials were performed. Results are tabulated in Table 1.

TABLE 1

| Trial number | Flow meter Drive voltage | Pump 1 speed, Hz | Pump 2 speed, Hz at calibration | Pump Control Voltages | Flow meter 1 speed, Hz * AVG | Flow meter 2 speed, Hz * AVG |
|---|---|---|---|---|---|---|
| 1 | 12.04 | 20.03 | 20.03 | [1].600 [2].612 | 66.95 | 68.10 |
| 2 | 12.04 | 20.02 | 20.02 | [1].600 [2].611 | 67.09 | 68.38 |
| 3 | 12.04 | 20.01 | 20.01 | [1].600 [2].611 | 67.33 | 68.01 |
| 4 | 12.04 | 20.01 | 20.00 | [1].599 [2].611 | 66.98 | 67.79 |
| 5 | 12.04 | 20.01 | 20.00 | [1].600 [2].611 | 66.88 | 67.73 |
| 6 | 12.04 | 20.03 | 20.03 | [1].601 [2].612 | 66.95 | 68.28 |
| 7 | 12.04 | 20.03 | 20.02 | [1].600 [2].612 | 66.70 | 68.45 |
| 8 | 12.04 | 20.03 | 20.03 | [1].600 [2].612 | 66.96 | 68.64 |
| 9 | 12.04 | 20.01 | 20.04 | [1].598 [2].611 | 67.36 | 68.62 |
| 10 | 12.04 | 20.04 | 20.01 | [1].600 [2].610 | 67.37 | 68.81 |

After obtaining data corresponding to a zero-UF condition for each trial, the line 62 was re-clamped using the second hemostat 60. The speed of the pump 34 was adjusted so as to obtain a pressure reading of 0 PSIG by the pressure gauge 64. After recording readings from all pumps and flowmeters, the first hemostat 58 was removed. After one minute, the gravimetric scale 66 supporting the second liquid vessel 52 was "tared". The second pump 34 was adjusted to obtain 0 mL/min flow from the second liquid vessel 52 (as monitored by the scale 66). The speed of the pump 34 was then increased to a desired value (5 trials performed with the second flowmeter 32 indicating about 70 Hz, and five trials performed with the second flowmeter indicating about 72 Hz); the scale 66 tared again, and the beginning of a 10-minute time duration was noted (using a stopwatch). During the time duration, readings from the flowmeters 20, 32 were continuously recorded. After the 10-minute period for each trial, a reading from the scale 66 was recorded to provide a measure of "ultrafiltration". Results are set forth in Table 2.

TABLE 2

| Trial number | Flow meter 1 speed, Hz (mean) | Flow meter 2 speed, Hz (mean) | Pump 1 speed, Hz | Pump 2 speed, Hz | Pump 2 Control voltage | Flow meter 1 speed, Hz (mean) | Flow meter 2 speed, Hz (mean) | Vol. removed |
|---|---|---|---|---|---|---|---|---|
| 1 | 65.52 | 66.60 | 20.01 | 19.94 | 0.669 | 65.63 | 70.08 | 256 g |
| 2 | 65.64 | 66.70 | 20.01 | 20.13 | 0.614 | 65.67 | 70.10 | 259 g |
| 3 | 66.54 | 66.79 | 20.01 | 20.30 | 0.620 | 67.85 | 69.96 | 260 g |
| 4 | 66.36 | 66.70 | 20.01 | 20.47 | 0.625 | 66.36 | 69.97 | 230 g |

TABLE 2-continued

| Trial number | Flow meter 1 speed, Hz (mean) | Flow meter 2 speed, Hz (mean) | Pump 1 speed, Hz | Pump 2 speed, Hz | Pump 2 Control voltage | Flow meter 1 speed, Hz (mean) | Flow meter 2 speed, Hz (mean) | Vol. removed |
|---|---|---|---|---|---|---|---|---|
| 5 | 66.47 | 66.99 | 20.01 | 20.59 | 0.625 | 66.54 | 70.15 | 220 g |
| 6 | 65.57 | 66.90 | 20.03 | 20.68 | 0.631 | 65.73 | 72.10 | 387 g |
| 7 | 65.70 | 67.22 | 20.02 | 20.84 | 0.636 | 65.76 | 72.10 | 357 g |
| 8 | 66.42 | 67.95 | 20.02 | 20.83 | 0.635 | 66.50 | 71.95 | 352 g |
| 9 | 65.67 | 67.42 | 19.98 | 20.56 | 0.626 | 65.71 | 72.00 | 367 g |
| 10 | 66.15 | 67.53 | 20.02 | 20.72 | 0.631 | 66.62 | 71.96 | 337 g |

The foregoing results indicate that the "ultrafiltrate" removed from the second vessel 52 is a function of the relative speeds of the pumps 14, 34 as indicated by the flowmeters 20, 32.

Whereas the invention has been described in connection with a preferred embodiment, it will be understood that the invention is not limited to such an embodiment. On the contrary, the invention is intended to encompass all alternatives, modifications, and equivalents as may be included within the spirit and scope of the invention as defined by the appended claims.

What is claimed is:

1. In a hemodialysis method, a method for priming a blood compartment of a hemodialyzer, the method comprising:

(a) providing a liquid;

(b) conducting the liquid through a first positive displacement pump, then through a first flowmeter, then to a dialysate inlet of a dialysate compartment of the hemodialyzer, the first pump delivering the liquid to the dialysate inlet at a first volumetric pumping rate as measured by the first flowmeter;

(c) after passing the liquid through the dialysate compartment, conducting the liquid from an outlet of the dialysate compartment through a second flowmeter, then through a second positive displacement pump, the second pump pumping the liquid at a second volumetric pumping rate, as measured by the second flowmeter, that is less than the pumping rate of the first pump so as to urge net flow of the liquid from the dialysate compartment to the blood compartment of the hemodialyzer.

2. The method of claim 1, wherein the liquid is a dialysate solution.

3. The method of claim 1, including the step of circulating the liquid through blood lines connected to the blood compartment of the hemodialyzer.

4. In a hemodialysis method, a method for priming a hemodialyzer comprising a dialysate compartment, a blood compartment, and a dialysis membrane separating the dialysate and blood compartments, the method comprising the steps:

(a) delivering a liquid to a dialysate inlet of the dialysate compartment at a first volumetric delivery rate;

(b) passing the liquid through the dialysate compartment from the dialysate inlet to a dialysate outlet of the hemodialyzer; and (c) delivering the liquid from the dialysate outlet at a second volumetric delivery rate that is less than the first volumetric delivery rate so as to cause a net flow of the liquid from the dialysate compartment to the blood compartment through the dialysis membrane.

5. The method of claim 4, further comprising the step of rinsing the blood compartment with the liquid entering the blood compartment through the dialysis membrane.

6. The method of claim 4, further comprising the step of causing the liquid entering the blood compartment through the dialysis membrane to flow into blood lines connected to the blood compartment.

7. The method of claim 6, further comprising the step of rinsing the blood compartment and blood lines with the liquid entering the blood compartment through the dialysis membrane.

8. The method of claim 4, wherein;

the step of delivering the liquid to the dialysate inlet comprises conducting the liquid through a first positive-displacement pump to the dialysate inlet; and the step of delivering the liquid away from the dialysate outlet comprises conducting the liquid from the dialysate outlet through a second positive-displacement pump.

9. The method of claim 8, wherein the first positive-displacement pump is caused to run at a first volumetric pumping rate, and the second positive-displacement pump is caused to run at a second volumetric pumping rate that is lower than the first volumetric pumping rate.

10. The method of claim 4, wherein the liquid is a dialysate solution.

11. The method of claim 4, including the step of measuring the net flow of liquid through the dialysis membrane.

12. In a hemodialysis method employing a hemodialyzer comprising a dialysate compartment, a blood compartment, and a dialysis membrane separating the dialysate and blood compartments, a method for adding a liquid to the blood compartment, the method comprising the steps:

(a) delivering a liquid to a dialysate inlet of the dialysate compartment at a first volumetric delivery rate;

(b) passing the liquid through the dialysate compartment from the dialysate inlet to a dialysate outlet of the hemodialyzer; and (c) delivering the liquid from the dialysate outlet at a second volumetric delivery rate that is less than the first volumetric delivery rate so as to cause a net flow of the liquid from the dialysate compartment to the blood compartment through the dialysis membrane.

13. In a hemodialysis method utilizing a hemodialyzer comprising a dialysate compartment, a blood compartment, and a dialysis membrane separating the dialysate and blood compartments, a method for delivering a filtered liquid into the blood compartment, the method comprising the steps:

(a) delivering a liquid to a dialysate inlet of the dialysate compartment at a first volumetric delivery rate;

(b) passing the liquid through the dialysate compartment from the dialysate inlet to a dialysate outlet of the hemodialyzer; and (c) delivering the liquid from the dialysate outlet at a second volumetric delivery rate that is less than the first volumetric delivery rate so as to cause a net flow of the liquid from the dialysate compartment through the dialysis membrane, whereby the liquid entering the blood compartment from the dialysate compartment is filtered by flowing through the dialysis membrane.

14. In a hemodialysis method utilizing a hemodialyzer comprising a dialysate compartment with an inlet and an outlet, a blood compartment, and a dialysis membrane separating the dialysate and blood compartments, a method for delivering a liquid into the blood compartment, the method comprising the steps:

(a) providing a ultrafiltration loop comprising a first volumetric delivery device and a second volumetric delivery device;

(b) connecting the dialysate compartment to the ultrafiltration loop by connecting the inlet of the dialysate compartment to an output of the first volumetric delivery device and connecting the outlet of the dialysate compartment to an inlet of the second volumetric delivery device;

(c) operating the first volumetric delivery device in a manner by which a liquid is delivered, from a source outside the ultrafiltration loop, at a first volumetric delivery rate by the first volumetric delivery device to the inlet of the dialysate compartment, thereby causing the liquid to flow through the dialysate compartment from the inlet to the outlet of the dialysate compartment; and (d) operating the second volumetric delivery device in a manner by which the liquid is delivered, from the outlet of the dialysate compartment, by the second volumetric delivery device at a second volumetric delivery rate that is less than the first volumetric delivery rate so as to cause a net flow of the liquid from the dialysate compartment to the blood compartment through the dialysis membrane.

15. The method of claim 14, wherein the liquid entering the blood compartment from the dialysate compartment is filtered by flowing through the dialysis membrane.

16. The method of claim 14, further comprising the steps of:

controlling operation of the first volumetric delivery device so as to control the first volumetric delivery rate; and controlling operation of the second volumetric delivery device so as to control the second volumetric delivery rate.

* * * * *

UNITED STATES PATENT AND TRADEMARK OFFICE
CERTIFICATE OF CORRECTION

PATENT NO. : 6,331,252 B1
DATED : December 18, 2001
INVENTOR(S) : El Sayyid et al.

It is certified that error appears in the above-identified patent and that said Letters Patent is hereby corrected as shown below:

Column 6,
Line 24, delete "38"

Signed and Sealed this

Twentieth Day of August, 2002

Attest:

Attesting Officer

JAMES E. ROGAN
Director of the United States Patent and Trademark Office